[19] United States Patent
Tollefsen et al.

[11] Patent Number: 5,102,995
[45] Date of Patent: Apr. 7, 1992

[54] DNA ENCODING MODIFIED HEPARIN COFACTOR II

[75] Inventors: Douglas M. Tollefsen; Vivianna M. Derechin; Morey A. Blinder, all of St. Louis, Mo.

[73] Assignee: Washington University, St. Louis, Mo.

[21] Appl. No.: 424,440

[22] Filed: Oct. 20, 1989

[51] Int. Cl.$^5$ ............................................. C12N 15/15
[52] U.S. Cl. .................................... 536/27; 435/214; 435/183; 935/10
[58] Field of Search ................ 536/27; 435/69.1, 69.6; 935/10

[56] References Cited

U.S. PATENT DOCUMENTS 4,849,349 7/1989 Ragg .................................. 435/69.2
4,861,865 8/1989 Hortin .................................. 530/326

OTHER PUBLICATIONS

Nakamonye et al., Nucl. Acid. Rev. (14):9679, 1986.
Owen et al., New Eng J. Med 309(12):694, 1983.
Derechin et al., J. Biol. Chem. (1990), 265:5623-5628.
Blinder et al., Biochemistry 27, 752-759 (1988).
Blinder et al., J. Biol. Chem. 264, 5128-5133 (1989).
Olins et al., Gene 73, 227-235 (1988).
Olins et al., J. Biol. Chem. 264, 16973-16976 (1989).
Church et al., Proc. Natl. Acad. Sci. U.S.A. 82, 6431-6434 (1985).
Griffith et al., J. Biol. Chem. 260, 2218-2225 (1985).
Griffith et al., Biochemistry 24, 6777-6782 (1985).
Carrell & Travis, TIBS 20, 20-24 (1985).

Primary Examiner—Richard A. Schwartz
Assistant Examiner—John L. LeGuyader
Attorney, Agent, or Firm—Scott J. Meyer; James W. Williams, Jr.

[57] ABSTRACT

A modified heparin cofactor II is disclosed, HCII (Leu$_{444}$→Arg), which has substantially improved inhibitory activity against thrombin compared to native HCII or antithrombin.

1 Claim, 5 Drawing Sheets

DNA ENCODING MODIFIED HEPARIN COFACTOR II

BACKGROUND OF THE INVENTION

This invention relates to heparin cofactor II and, more particularly, to a modified heparin cofactor II that has substantially improved inhibitory activity against thrombin compared to native heparin cofactor II or antithrombin.

The anticoagulant activities of glycosaminoglycans are mediated by antithrombin (AT) and heparin cofactor II (HCII), which are members of the 'serpin' family of serine protease inhibitors [Tollefsen in *Heparin: chemical and biological properties, clinical applications* (eds. Lane and Lindahl), Edward Arnold, London, 1989, pp. 257-273]. HCII inhibits thrombin but has no activity against other proteases involved in coagulation or fibrinolysis [Parker and Tollefsen, *J. Biol. Chem.* 260, 3501-3505 (1985)]. In contrast, AT inhibits all of the proteases of the intrinsic coagulation pathway as well as the fibrinolytic protease plasmin [Rosenberg in The molecular basis of blood diseases (eds. Stamatoyannopoulos et al.), W. B. Saunders Co., Philadelphia, 1987, pp. 534-574]. Heparin and dermatan sulfate increase the rate of thrombin inhibition by HCII ~1000-fold by providing a catalytic template to which both the inhibitor and the protease bind [Tollefsen et al., *J. Biol. Chem.* 258, 6713-6716 (1983); Griffith, *Proc. Natl. Acad. Sci. USA* 80, 5460-5464 (1983)]. Although heparin catalyzes protease inhibition by both HCII and AT, the anticoagulant effect of dermatan sulfate is mediated exclusively by HCII.

HCII is a 65,600 dalton plasma glycoprotein. Using conventional recombinant DNA gene splicing methods, the cDNA sequence and corresponding amino acid sequence of HCII were determined and the protein was expressed in *E. coli* by Blinder et al., *Biochemistry* 27, 752-759 (1988). The cDNA consisted of 2215 base pairs (bp), including an open-reading frame of 1525 bp, a stop codon, a 3'-noncoding region of 654 bp, and a poly(A) tail. The deduced amino acid sequence contained a signal peptide of 19 amino acid residues and a native protein of 480 amino acids. The published cDNA and protein sequences are also shown hereinbelow.

HCII forms a stable 1:1 complex with thrombin or chymotrypsin in which the protease is inactive. During complex formation, both thrombin and chymotrypsin attack the reactive site $Leu_{444}$-$Ser_{445}$ peptide bond (designated P1-P1') near the C-terminal end of HCII [Church et al., *Proc. Natl. Acad. Sci. USA* 82, 6431-6434 (1985); Griffith et al., *J. Biol. Chem.* 260, 2218-2225 (1985); Griffith et al., *Biochemistry* 24, 6777-6782 (1985)]. The resulting complex does not dissociate when heated at 100° C. with sodium dodecyl sulfate, suggesting that under these conditions the two proteins become linked by a covalent bond. The bond is presumed to be an ester linkage between the serine hydroxyl group in the active site of the protease and the carbonyl group of $Leu_{444}$ in HCII. Therefore, HCII can be thought of as a pseudosubstrate for these proteases.

The P1 residue in the reactive site of a 'serpin' appears to play a major role in determining the relative rates of inhibition of various proteases [Carrell and Travis, *TIBS* 10, 20-24 (1985)]. Evidence for this was derived from analysis of the variant α1-antitrypsin Pittsburgh, which was discovered in a child who had a fatal bleeding disorder. The variant contained an arginine residue in place of $Met_{358}$ at the P1 position of the inhibitor [Owen et al., *N. Engl. J. Med.* 309, 694-698 (1983)]. This substitution resulted in markedly increased rates of inhibition of several coagulation proteases, including thrombin, factor Xa, factor XIa, and kallikrein, which cleave Arg-X peptide bonds in their natural substrates [Schapira et al., *J. Clin. Invest.* 77, 635-637 (1986); Scott et al., *Ibid.* 77, 631-634 (1986); Travis et al., *Biol. Chem. Hoppe-Seyler* 367, 853-859 (1986)]. A reciprocal decrease in the rate of inhibition of neutrophil elastase, the principal target protease of native α1-antitrypsin, was also noted.

Heparin is commonly employed in the prophylaxis and treatment of venous thrombosis and pulmonary embolism, but its use is sometimes complicated by severe bleeding or thrombocytopenia. Therefore, alternatives to heparin for short-term anticoagulation would be desirable. In this regard, a modified HCII which could inhibit thrombin rapidly in the absence of heparin would have significant value and be useful for the treatment of thrombotic disorders.

BRIEF DESCRIPTION OF THE INVENTION

In accordance with the present invention a novel modified HCII has been developed which has substantially improved inhibitory activity against thrombin compared to native HCII or antithrombin. These improved results of about 100-fold increased inhibitory activity were unexpected in view of the single site mutation of the native HCII which characterizes the novel modified HCII. For convenience, the modified HCII of this invention can be represented as HCII($Leu_{444} \rightarrow Arg$). In this mutation, the leucine residue at position 444 is replaced by a positively charged arginine in the published 480 amino acid sequence of native HCII.

The modified HCII($Leu_{444} \rightarrow Arg$) of this invention inhibited thrombin at a 98-fold higher rate ($k_2 = 6.2 \times 10^6$ M$^{-1}$min$^{-1}$) than native HCII ($k_2 = 6.3 \times 10^4$ M$^{-1}$min$^{-1}$). Dermatan sulfate accelerated thrombin inhibition by both the native and modified forms of HCII, but the maximum rate constant in the presence of dermatan sulfate was only 2-fold higher for HCII($Leu_{444} \rightarrow Arg$)($k_2 = 5.3 \times 10^8$ M$^{-1}$min$^{-1}$) than for native HCII ($k_2 = 2.2 \times 10^8$ M$^{-1}$min$^{-1}$). Heparin was less effective than dermatan sulfate in stimulating both forms of HCII. Factor Xa and kallikrein were inhibited more rapidly and chymotrypsin more slowly by HCII($Leu_{444} \rightarrow Arg$) than by native HCII. The rapid rate of inhibition of thrombin by HCII($Leu_{444} \rightarrow Arg$) in the absence of heparin or dermatan sulfate suggests that this variant may be useful as a therapeutic agent.

The single site mutation of HCII as defined herein is illustrated in a recombinant HCII (rHCII). However, the amino acid sequence of rHCII is identical to that of HCII purified from human plasma. Thus, as defined herein the single site mutation HCII($Leu_{444} \rightarrow Arg$) can be made on a recombinant HCII or a synthetically produced HCII.

Conventional recombinant DNA procedures can be used to prepare the novel HCII mutant of this invention. The starting material can be a conventional DNA construct or vector comprising a DNA sequence encoding for the entire sequence of native HCII. The reactive site mutant rHCII($Leu_{444} \rightarrow Arg$) is then prepared by replacing the codon for leucine at site 444 with the codon for arginine.

Thus, the DNA polymer can be prepared by the enzymatic ligation of chemically synthesized fragments. The DNA polymer which encodes the modified HCII may be prepared by site-directed mutagenesis of the cDNA which codes for HCII by conventional methods such as those described by Winter et al., *Nature* 299, 756–758 (1982) or Zoller and Smith, *Nucl. Acids Res.* 10, 6487–6500 (1982). Expression of the modified HCII can be carried out by conventional methods.

A suitable starting material for preparing the HCII($Leu_{444} \rightarrow Arg$) of this invention is the known plasmid expression vector pMON-5840 as described by Blinder et al., *J. Biol. Chem.* 264, 5128–5133 (1989). This plasmid is a variant of pMON5527 which, in addition to an irrelevant sequence, contains the recA promoter ($P_{rec}A$) and the ribosome-binding site, T7 phage gene 10 leader RNA (G10-L RBS), and is suitable for enhanced expression of foreign genes in *E. coli*, as further described by Olins et al., *Gene* 73, 227–235 (1988); Olins and Rangwala, *J. Biol. Chem.* 264, 16973–16976 (1989). The recA promoter in pMON-5840 is derived as the HpaII fragment and corresponds to nucleotides 63-210 of the sequence published by Horii et al., *Proc. Natl. Acad. Sci. USA* 77, 313–317 (1980). The cDNA for HCII($Leu_{444} \rightarrow Arg$) can be ligated into the parent vector which can then be used for expression of the rHCII($Le_{444} \rightarrow Arg$) by conventional procedures, e.g. in *E. coli* JM101 cells.

DETAILED DESCRIPTION OF THE INVENTION

Figure 1:
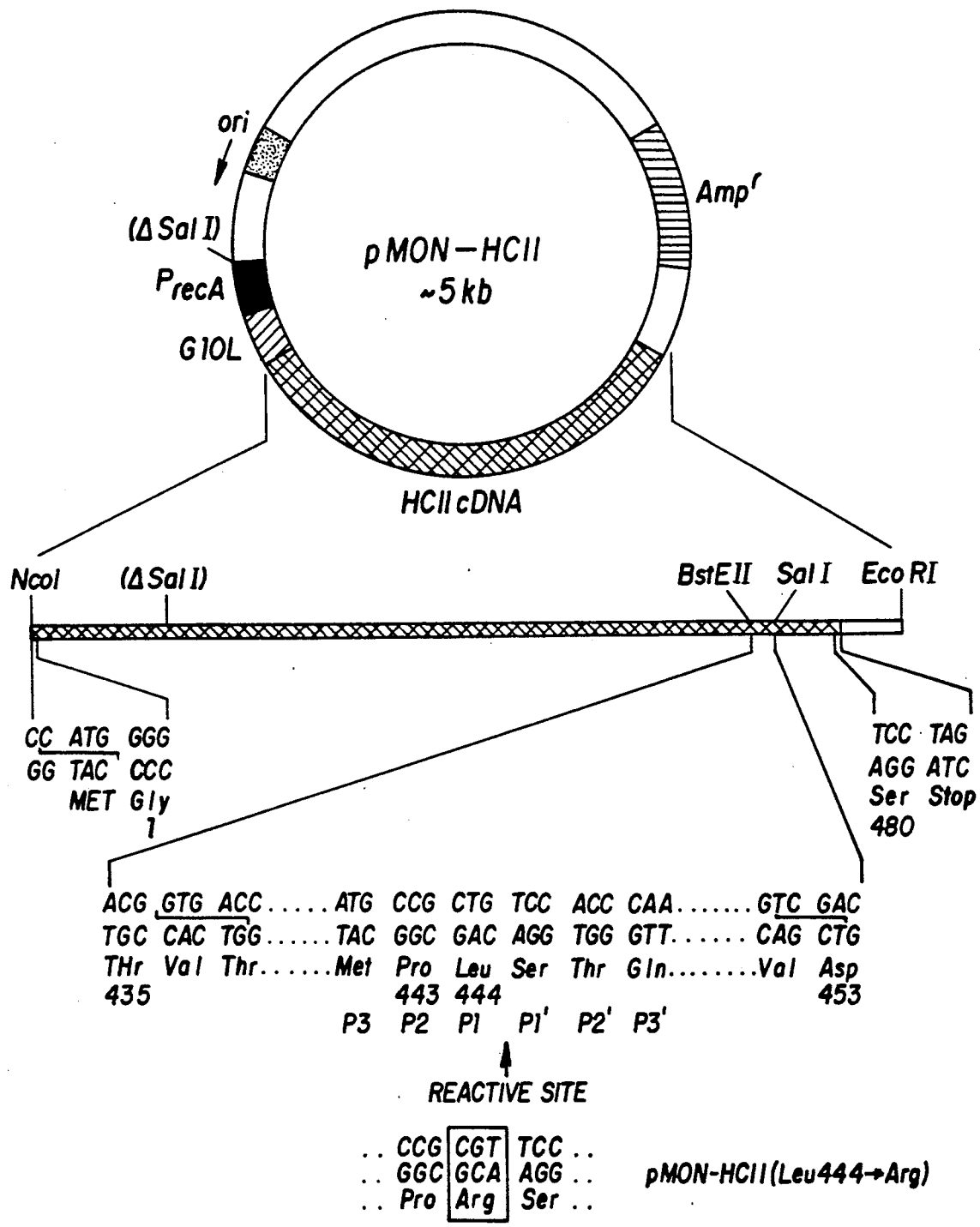

While the specification concludes with claims particularly pointing out and distinctly claiming the subject matter regarded as forming the present invention, it is believed that the invention will be better understood from the following detailed description of preferred embodiments of the invention taken in conjuction with the appended drawings in which:

FIG. 1 is a schematic diagram of the expression vector pMON-HCII. HCII cDNA (shaded rectangle) was altered in M13 to remove a SalI site and create a BstEII site. Cassette mutagenesis between BstEII and SalI was performed to create the reactive site mutant pMON-HCII($Leu_{444} \rightarrow Arg$). The open rectangle denotes the 3'-untranslated sequence from the HCII cDNA. The RecA promoter (P recA) and G10L translational control element, derived from the T7 gene, are indicated, along with the deletion of a SalI site in the parent vector pMON-5840. The codons and amino acids at the translation initiation site and in the reactive site cassette are shown.

Figure 2:
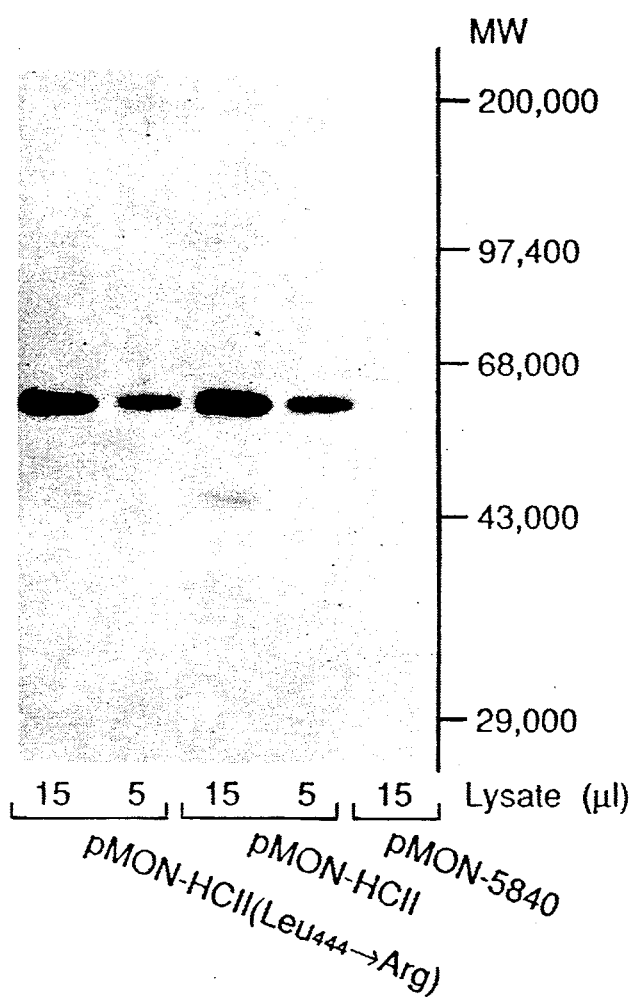
Figure 3A:
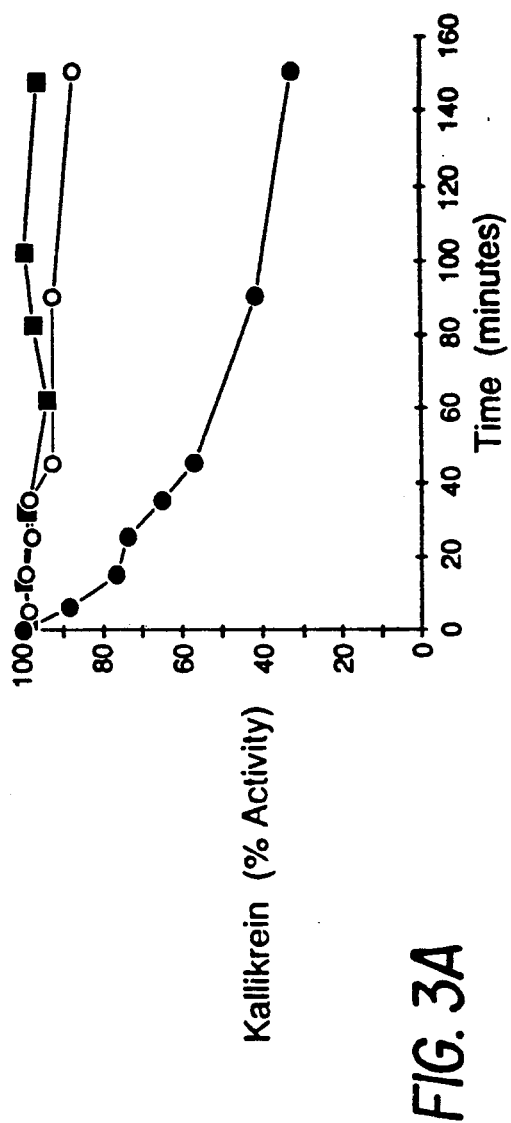
Figure 3B:
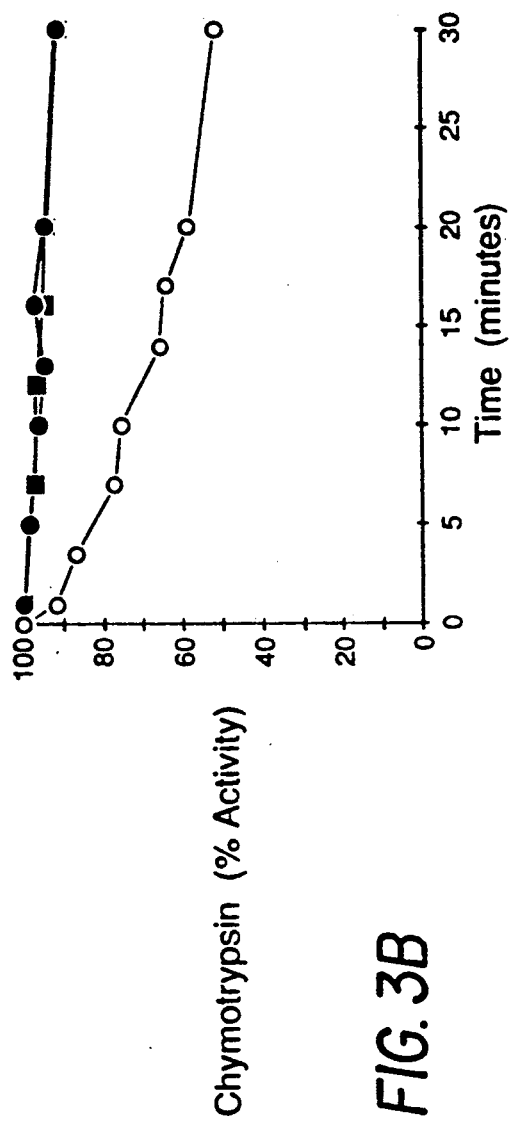
Figure 3C:
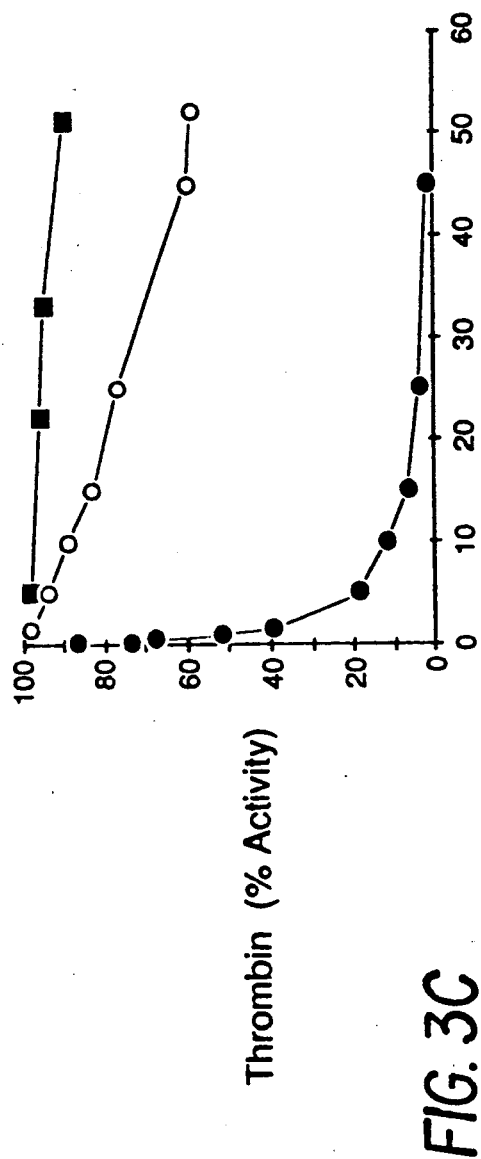
Figure 3D:
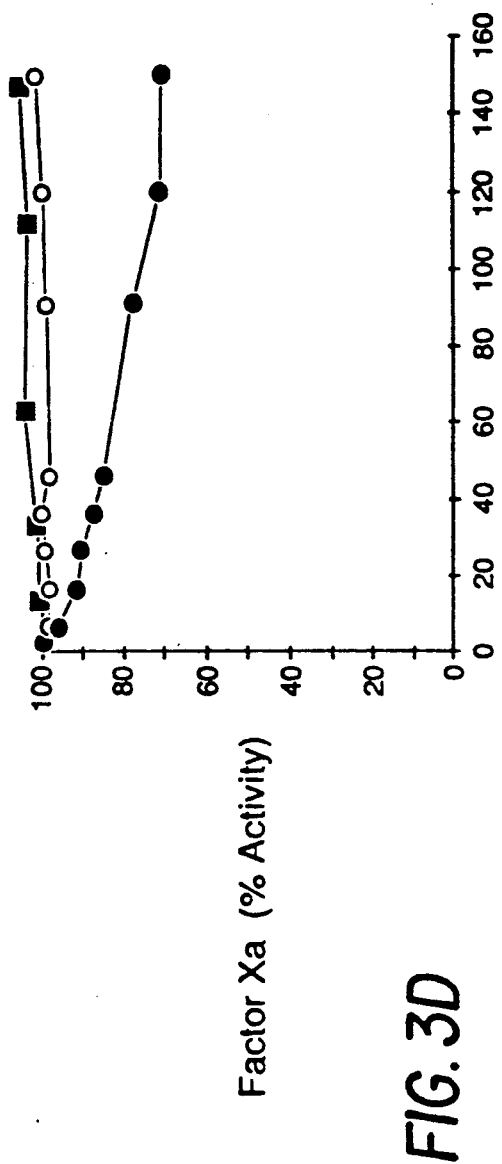

FIG. 2 shows the immunoblot of pMON-HCII, pMON-HCII($Leu_{444} \rightarrow Arg$) and pMON-5840 lysates with anti-HCII antibody. pMON-HCII, pMON-HCII($Leu_{444} \rightarrow Arg$) and pMON-5840 were expressed in *E. coli* and subjected to heparin-Sepharose ® chromatography, as described below under "Procedures." The partially purified rHCII, rHCII($Leu_{444} \rightarrow Arg$) and control lysate were immunoblotted and probed with $^{125}$I-labelled rabbit anti-HCII antibodies. An autoradiograph of the immunoblot is shown. The amount (μl) of partially purified lysate loaded in each lane is indicated. Molecular weight markers are shown on the right hand side.

FIG. 3 (parts A-D) is a graphical representation which shows the inhibition of thrombin, chymotrypsin, factor Xa and kallikrein by rHCII and rHCII($Leu_{444} \rightarrow Arg$). Heparin-Sepharose column eluates (90 μl) of rHCII (142 nM), rHCII($Leu_{444} \rightarrow Arg$) (76 nM) or pMON-5840 control were incubated with thrombin (15 nM), chymotrypsin (21 nM), factor Xa (16 nM), or kallikrein (10 nM) for the indicated amount of time at the stated final concentrations. The % protease activity was calculated from the ratio of final to initial protease activity, determined by adding the appropriate chromogenic substrate and measuring Δ405/min as described below under "Procedures." ●, Control; ○, Native rHCII; ●, rHCII($Leu_{444} \rightarrow Arg$).

Figure 4:
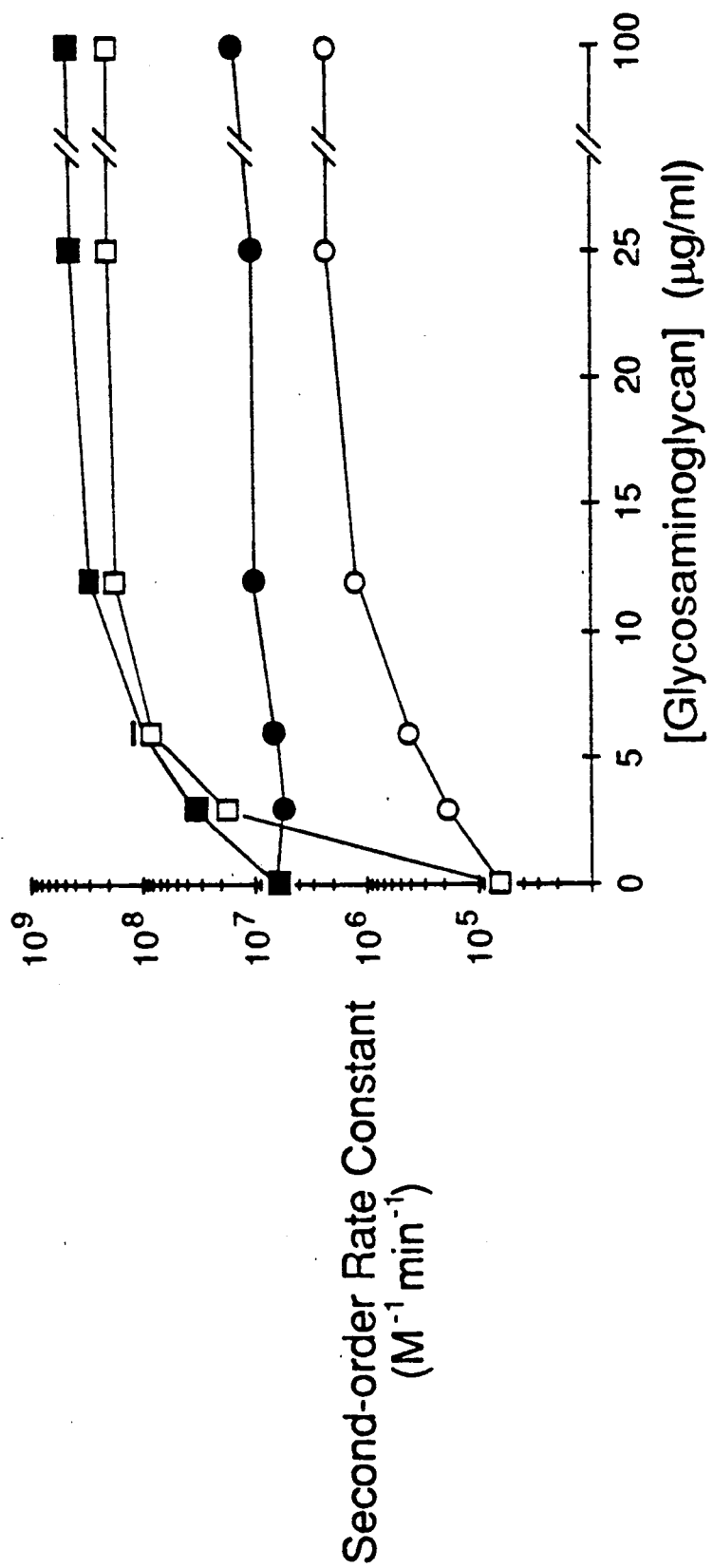

FIG. 4 is a graphical representation which shows the effect of glycosaminoglycan concentration on the second-order rate constant of thrombin inhibition by rHCII and rHCII($Leu_{444} \rightarrow Arg$). Second-order rate constants were determined by incubating heparin-Sepharose column eluates (90 μl) of rHCII (142 nM) or rHCII($Leu_{444} \rightarrow Arg$) (76 nM) with thrombin (15 nM) and either heparin or dermatan sulfate at the indicated final concentrations. The rate constants were calculated as described below under "Procedures." After times ranging from 5 seconds to 5 minutes remaining thrombin activity was determined by adding Chromozym TH and measuring Δ405/min. The rate constants with dermatan sulfate are the average of three similar tests. The heparin-stimulated rate constants are from a single determination. ○, rHCII plus heparin; ●, rHCII($Leu_{444} \rightarrow Arg$) plus heparin; □, rHCII plus dermatan sulfate; ●, rHCII($Lue_{444} \rightarrow Arg$) plus dermatan sulfate.

In order to illustrate the invention in greater detail, the following exemplary laboratory preparative work was carried out and the results obtained as described and shown in Table 1 and the accompanying drawings.

EXAMPLES

Procedures

Materials—Chromogenic substrates were purchased from the following sources: tosyl-Gly-Pro-Arg-p-nitroanilide (Chromozym TH), Boehringer Mannheim; N-succinyl-Ala-Ala-Pro-Phe-p-nitroanilde, Sigma; methoxycarbonyl cyclohexylglycyl-Gly-Arg-p-nitroanilde (Spectrozyme FXa), American Diagnostica; and Pro-Phe-Arg-p-nitroanilide (S-2302), KabiVitrum. Thrombin and HCII derived from human plasma were prepared and assayed by conventional procedures as previously described by Blinder et al., *J. Biol. Chem.* 264, 5128–5133 (1989). Human coagulation factor $X_a$ was provided by Dr. George Broze, Jr., Washington University, St. Louis, Mo. Human chymotrypsin and plasma kallikrein were purchased from Sigma. Affinity purified rabbit anti-HCII antibodies were prepared and labeled with Na[$^{125}$I] by conventional procedure as described previously by Blinder et al., *Biochemistry* 27, 752–759 (1988). Bovine lung heparin and porcine skin dermatan sulfate were purchased from Sigma; the dermatan sulfate was treated with nitrous acid to remove contaminating heparin prior to use [Teien et al., *Thromb. Res.* 8, 859–867 (1976)]. Heparin-Sepharose was prepared by commonly known procedure as described previously by Tollefsen et al., *J. Biol. Chem.* 257, 2162–2169 (1982).

The reagents used for oligonucleotide directed mutagenesis were purchased from Amersham. Restriction enzymes were obtained from Promega, Amersham, New England Biolabs, and Bethesda Research Laboratories. Reagents for the Taq polymerase chain reaction were purchased from Perkin Elmer Cetus. DNA sequencing was performed using T7 DNA polymerase from U.S. Biochemical Corporation. Deoxyadenosine

[α$^{35}$S]thiotriphosphate([α$^{35}$S]dATP) was obtained from Dupont-New England Nuclear. The Protein Chemistry Facility of Washington University, St. Louis, Mo., provided the synthetic oligonucleotides.

Construction of the pMON-HCII expression vector—Previously, the PstI-HindIII fragment of the HCII cDNA was inserted into pMON-5840 to yield a construct in which the N-terminal 18 amino acid residues of mature plasma HCII were replaced by the sequence Met-Ala- as described by Blinder et al., *J. Biol. Chem.* 264, 5128-5133 (1989). Although the resulting inhibitor was active by several criteria, it was desired to obtain a full-length rHCII for the purposes of the present invention. In addition, it was decided to construct unique SalI and BstEII restriction sites for cassette mutagenesis of the reactive site. The SalI site in the parent vector pMON-5840 was deleted to form pMON-5840(ΔSalI) by digestion with SalI, treatment with mung bean exonuclease, and religation. A full-length cDNA for HCII was isolated previously from a human fetal liver library in λgt11 as described by Blinder et al., *Biochemistry* 27, 752-759 (1988). Oligonucleotide-directed mutagenesis of the cDNA was performed in M13mp18 phage vector containing the non-coding strand by the published method of Nakamaye and Eckstein, *Nucl. Acids Rev.* 14, 9679-9698 (1986). The codon for Val$_{77}$ was altered (GTC→GTT) to remove a SalI site at that position, and the codon for Thr$_{434}$ was altered (ACT→ACG) to construct a BstEII site. Using the polymerase chain reaction with appropriate primers [Saiki et al., *Science* 239, 487-491 (1988)], an NcoI site (CCATGG) was incorporated into the cDNA so that the ATG of the NcoI site immediately preceded the codon for Gly$_1$ of mature plasma HCII. The amplified cDNA was then ligated into pMON-5840(ΔSalI). The final construct, designated pMON-HCII, is diagrammed in FIG. 1.

Cassette mutagenesis of pMON-HCII—pMON-HCII was digested with SalI and BstEII to remove a fragment of DNA containing the codons for Val$_{436}$-Val$_{452}$, which span the reactive site. The vector was then treated with alkaline phosphatase. Complementary oligonucleotides (48- and 49-mers) containing the codon for arginine at position 444 were phosphorylated with T4 kinase, preannealed, and then ligated to the vector. *E. coli* strain JM101 cells were transformed with the vector, and colonies were selected for ampicillin resistance. The sequence of the final plasmid was verified using the dideoxy chain termination method of Sanger et al., *Proc. Natl. Acad. Sci. USA* 74, 5463-5467 (1977).

Expression and quantification of native rHCII and rHCII(Leu$_{444}$→Arg)—For each rHCII preparation, transformed *E. coli* were grown to an optical density (550 nm) of 1.0-1.2 in 500 ml of medium and expresiion was induced with nalidixic acid according to Li et al., *J. Biol. Chem.* 262, 13773-13779 (1987). The cells were then sedimented, rinsed once in 0.05M NaCl, 0.05M Tris-HCl, pH 7.5, resuspended in 25 ml of the same buffer, and lysed by sonication [Blinder et al., *Biochemistry* 27, 752-759 (1988)]. To partially purify the rHCII, the cell lysate was applied to a 30 ml column of heparin-Sepharose equilibrated with the same buffer. After the column was washed, the rHCII was eluted with 1.0M NaCl, 0.05M Tris-HCl, pH 7.5. The eluate was dialyzed against 0.05M NaCl, 0.05M Tris-HCl, pH 7.5, and stored frozen.

The concentration of rHCII was determined by a slot blot immunoassay. Various amounts of the partially purified rHCII were blotted onto nitrocellulose, and rHCII was detected with $^{125}$I-labeled anti-HCII antibodies as described previously by Blinder et al., Ibid. After autoradiography, the bands were scanned with a densitometer and the areas under each peak were determined (LKB Ultroscan). A standard curve constructed with known amounts of plasma HCII was linear from 2.5 to 30 ng. The standard deviation of multiple determinations of plasma HCII using this method was 20%.

Inhibition of proteases by rHCII—Protease inhibition by rHCII was determined by incubating 90 μl of the partially purified rHCII (or the corresponding heparin-Sepharose fractions of a control lysate from cells transformed with pMON-5840) with 5 μl of the protease and 5 μl of either glycosaminoglycan or water in a disposable polystyrene cuvette at room temperature. Final concentrations of the proteases were as follows: thrombin, 15 nM; chymotrypsin, 21 nM; factor Xa, 16 nM; and kallikrein, 10 nM. After a specified period of time from 5 seconds (s) to 150 min, 300-500 μl of the appropriate chromogenic substrate was added, and the absorbance at 405 nm was recorded continuously for 100 s. The rate of change of absorbance was proportional to the concentration of active protease remaining in the incubation. The amounts added and concentrations of each substrate were as follows: Chromozym TH (thrombin), 500 μl, 0.1 mM; N-succinyl-Ala-Ala-Pro-Phe-p-nitroanilde (chymovtrypsin), 300 μl, 0.5 mM; Spectrozyme FX$_a$ (factor Xa), 400 μl, 0.125 mM; and S-2302 (kallikrein), 300 μl, 0.4 mM.

Results

Expression vectors for rHCII—A diagram of the HCII expression vector (pMON-HCII) is shown in FIG. 1. The mRNA produced by this vector contains an initiator Met codon followed by the nucleotide sequence encoding the mature polypeptide (i.e., minus signal peptide) of native HCII. Edman degradation of rHCII purified from a cell lysate revealed that the sequence begins with Gly:, indicating that the initiating Met residue is removed during biosynthesis in *E. coli*. Thus, the amino acid sequence of native rHCII is identical to that of HCII purified from human plasma. The reactive site mutant rHCII(Leu$_{444}$→Arg) was prepared by insertion of the appropriate synthetic oligonucleotide cassette into pMON-HCII digested with BstEII and SalI as indicated in FIG. 1.

Immunoblot and quantification of rHCII—FIG. 2 shows the autoradiograph of an immunoblot of lysates of *E. coli* transformed with pMON-5840 (parent vector lacking the HCII cDNA), pMON-HCII, or pMON-HCII(Leu$_{444}$→Arg). Each lysate was subjected to heparin-Sepharose chromatography as described above under "Procedures" prior to immunoblotting. The immunoblot was probed with $^{125}$I-labeled rabbit anti-HCII antibodies. The figure indicates that the rHCII expressed by pMON-HCII(Leu$_{444}$→Arg) is identical in size to that expressed by pMON-HCII and has an apparent molecular weight of ~60,000. A minor band (MW=43,000) containing 5-10% of the HCII antigen is also present in both lysates and may represent a degraded form of the protein. No HCII antigen is present in a lysate of *E. coli* transformed with pMON-5840. The level of expression of rHCII was determined by densitometry of immunoblots standardized with known amounts of purified plasma HCII. The rHCII concentration in the pMON-HCII and pMON-HCII(Leu$_{444}$→Arg) lysates (after heparin-Sepharose chromatography) were 158 nM and 84 nM, respectively.

Protease inhibition by rHCII in the absence of a glycosaminoglycan—The time courses of inhibition of thrombin, factor Xa, kallikrein, and chymotrypsin by native rHCII(Leu$_{444}$→Arg) in the absence of a glycosaminoglycan are indicated in FIG. 3. The incubations were performed under pseudo-first-order conditions, such that the initial concentration of rHCII was greater than the concentration of protease. The pseudo-first-order rate constants ($k_1$) for protease inhibition were determined by fitting the data to the following equation: $k_1 t = \ln([P]_0/[P]_t)$, in which $[P]_0$ = initial protease activity and $[P]_t$ = protease activity at time = t. The second-order rate constants ($k_2$) were then calculated by dividing $k_1$ by the initial rHCII concentration. The rate constants are summarized in Table 1. It was observed that rHCII(Leu$_{444}$→Arg) inhibits thrombin almost 100 times more rapidly than native rHCII in the absence of a glycosaminoglycan. Furthermore, rHCII(Leu$_{444}$→Arg) inhibits factor Xa and kallikrein, while inhibition of these proteases by native rHCII is undetectable. In contrast to native rHCII, rHCII(Leu$_{444}$→Arg) does not inhibit chymotrypsin at a detectable rate.

Inhibition of thrombin by rHCII in the presence of dermatan sulfate or heparin—The time course of inhibition of thrombin was determined in the presence of various concentrations of dermatan sulfate or heparin. The second-order rate constants derived from these tests are shown in FIG. 4. Maximum rate constants were observed at 25–100 μg/ml of either glycosaminoglycan (Table 1). Dermatan sulfate produces approximately a 3500-fold increase in the rate constant for thrombin inhibition by native rHCII but has a much smaller effect on the rate constant obtained with rHCII(Leu$_{444}$→Arg). Thus, rHCII(Leu$_{444}$→Arg) inhibits thrombin only about twice as fast as native rHCII in the presence of dermatan sulfate. Heparin increases the rate constant for thrombin inhibition by native rHCII about 40-fold but has a minimal effect on the rate constant obtained with rHCII(Leu$_{444}$→Arg).

Inhibition of chymotrypsin, factor Xa and kallikrein by rHCII in the presence of dermatan sulfate or heparin—Dermatan sulfate does not significantly increase the rate of inhibition of chymotrypsin by native rHCII, nor does it increase the rate of inhibition of factor Xa or kallikrein by rHCII(Leu$_{444}$→Arg) (Table 1). Heparin (100 μg/ml) appears to protect factor Xa and kallikrein from inhibition by rHCII(Leu$_{444}$→Arg).

TABLE 1

| | Second-order rate constants ($k_2$) for inhibition of proteases by rHCII | | | | | |
|---|---|---|---|---|---|---|
| | native rHCII | | | rHCII(Leu$_{444}$→Arg) | | |
| Protease | No GAG | + Dermatan Sulfate | + Heparin | No GAG | + Dermatan Sulfate | + Heparin |
| | $k_2 (M^{-1} min^{-1})$ | | | | | |
| Thrombin | $6.3 \times 10^4$ [a] | $2.2 \times 10^8$ [b] | $2.4 \times 10^6$ [c] | $6.2 \times 10^6$ [a] | $5.3 \times 10^8$ [b] | $1.6 \times 10^7$ [c] |
| Chymotrypsin | $2.2 \times 10^5$ [a] | $3.7 \times 10^5$ [c] | $2.4 \times 10^5$ [c] | $<1 \times 10^4$ [b] | $<1 \times 10^4$ [c] | N.D. |
| Factor Xa | $<1 \times 10^3$ [b] | $<1 \times 10^3$ [b] | N.D. | $4.4 \times 10^4$ [c] | $6.2 \times 10^4$ [b] | $2.1 \times 10^4$ [b] |
| Kallikrein | $<3 \times 10^3$ [c] | N.D. | N.D. | $1.3 \times 10^5$ [c] | $1.4 \times 10^5$ [c] | $1.0 \times 10^4$ [c] |

The rate constants were determined as described above under "Procedures" and are derived from the data in FIGS. 2 and 3. The maximum rate constants obtained in the presence of 25–100 μg/ml of dermatan sulfate or heparin are given.
GAG, glycosaminoglycan.
N.D., not determined.
[a] Average of three determinations.
[b] Average of two determinations.
[c] Single determination.

Heparin Cofactor II

```
            -19                                                      -11
            Met Lys His Ser Leu Asn Ala Leu Leu Ile Phe Leu Ile  Ile
CGAAACACAGAGCTTTAGCTCCGCCAAAATG AAA CAC TCA TTA AAC GCA CTT CTC ATT TTC CTC ATC ATA
1                                                                         50

-1  +1                                           10
Thr Ser Ala Trp Gly Gly Ser Lys Gly Pro Leu Asp Gln Leu Glu Lys Gly Gly Glu Thr Ala Gln
ACA TCT GCG TGG GGT GGG AGC AAA GGC CCG CTG GAT CAG CTA GAG AAA GGA GGG GAA ACT GCT CAG
                                       100

20                                    CHO
Ser Ala Asp Pro Gln Trp Glu Gln Leu Asn Asn Lys Asn Leu Ser Met Pro Leu Leu Pro Ala Asp
TCT GCA GAT CCC CAG TGG GAG CAG TTA AAT AAC AAA AAC CTG AGC ATG CCT CTT CTC CCT GCC GAC
                      150                                             200

40                       50                                           SO4
Phe His Lys Glu Asn Thr Val Thr Asn Asp Trp Ile Pro Glu Gly Glu Glu Asp Asp Asp Tyr Leu
TTC CAC AAG GAA AAC ACC GTC ACC AAC GAC TGG ATT CCA GAG GGG GAG GAG GAC GAC GAC TAT CTG
                                                   250

70             SO4                   80
Asp Leu Glu Lys Ile Phe Ser Glu Asp Asp Asp Tyr Ile Asp Ile Val Asp Ser Leu Ser Val Ser
GAC CTG GAG AAG ATA TTC AGT GAA GAC GAC GAC TAC ATC GAC ATC GTC GAC AGT CTG TCA GTT TCC
                                      300
```

-continued
Heparin Cofactor II

```
                      90                                              100
Pro Thr Asp Ser Asp Val Ser Ala Gly Asn Ile Leu Gln Leu Phe His Gly Lys Ser Arg Ile
CCG ACA GAC TCT GAT GTG AGT GCT GGG AAC ATC CTC CAG CTT TTT CAT GGC AAG AGC CGG ATC
                        350

110                                         120
Gln Arg Leu Asn Ile Leu Asn Ala Lys Phe Ala Phe Asn Leu Tyr Arg Val Leu Lys Asp Gln Val
CAG CGT CTT AAC ATC CTC AAC GCC AAG TTC GCT TTC AAC CTC TAC CGA GTG CTG AAA GAC CAG GTC
  400                                                                          450

130                                   140
Asn Thr Phe Asp Asn Ile Phe Ile Ala Pro Val Gly Ile Ser Thr Ala Met Gly Met Ile Ser Leu Gly
AAC ACT TTC GAT AAC ATC TTC ATA GCA CCC GTT GGC ATT TCT ACT GCG ATG GGT ATG ATT TCC TTA GGC
                                             500

150                                      160                                   CHO 170
Leu Lys Gly Glu Thr His Glu Gln Val His Ser Ile Leu His Phe Lys Asp Phe Val Asn Ala Ser
CTG AAG GGA GAG ACC CAT GAA CAA GTG CAC TCG ATT TTG CAT TTT AAA GAC TTT GTT AAT GCC AGC
                      550

180                                            190
Ser Lys Tyr Glu Ile Thr Thr Ile His Asn Leu Phe Arg Lys Leu Thr His Arg Leu Phe Arg Arg
AGC AAG TAT GAA ATC ACG ACC ATT CAT AAT CTC TTC CGT AAG CTG ACT CAT CGC CTC TTC AGG AGG
  600                                                            650

200                                     210
Asn Phe Gly Tyr Thr Leu Arg Ser Val Asn Asp Leu Tyr Ile Gln Lys Gln Phe Pro Ile Leu Leu Asp
AAT TTT GGG TAC ACA CTG CGG TCA GTC AAT GAC CTT TAT ATC CAG AAG CAG TTT CCA ATC CTG CTT GAC
                                       700

220                                    230
Phe Arg Thr Lys Val Arg Glu Tyr Tyr Phe Ala Glu Ala Gln Ile Ala Asp Phe Ser Asp Pro Ala
TTC AGA ACT AAA GTA AGA GAG TAT TAC TTT GCT GAG GCC CAG ATA GCT GAC TTC TCA GAC CCT GCC
                     750

240                                   250                                 260
Phe Ile Ser Lys Thr Asn Asn His Ile Met Lys Leu Thr Lys Gly Leu Ile Lys Asp Ala Leu Glu
TTC ATA TCA AAA ACC AAC AAC CAC ATC ATG AAG CTC ACC AAG GGC CTC ATA AAA GAT GCT CTG GAG
800                                                         ·        850

270                                        280
Asn Ile Asp Pro Ala Thr Gln Met Met Ile Leu Asn Cys Ile Tyr Phe Lys Gly Ser Trp Val Asn
AAT ATA GAC CCT GCT ACC CAG ATG ATG ATT CTC AAC TGC ATC TAC TTC AAA GGA TCC TGG GTG AAT
                                          900

290                                        300
Lys Phe Pro Val Glu Met Thr His Asn His Asn Phe Arg Leu Asn Glu Arg Glu Val Val Lys Val
AAA TTC CCA GTG GAA ATG ACA CAC AAC CAC AAC TTC CGG CTG AAT GAG AGA GAG GTA GTT AAG GTT
                        950

310                                     320
Ser Met Met Gln Thr Lys Gly Asn Phe Leu Ala Ala Asn Asp Gln Glu Leu Asp Cys Asp Ile Leu
TCC ATG ATG CAG ACC AAG GGG AAC TTC CTC GCA GCA AAT GAC CAG GAG CTG GAC TGC GAC ATC CTC
  1000

330                                   340
Gln Leu Glu Tyr Val Gly Gly Ile Ser Met Leu Ile Val Val Pro His Lys Met Ser Gly Met Lys
CAG CTG GAA TAC GTG GGG GGC ATC AGC ATG CTA ATT GTG GTC CCA CAC AAG ATG TCT GGG ATG AAG
                                         1100

350                                     360                              CHO   370
Thr Leu Glu Ala Gln Leu Thr Pro Arg Val Val Glu Arg Trp Gln Lys Ser Met Thr Asn Arg Thr
ACC CTC GAA GCG CAA CTG ACA CCC CGG GTG GTG GAG AGA TGG CAA AAA AGC ATG ACA AAC AGA ACT
                          1150

380                                           390
Arg Glu Val Leu Leu Pro Lys Phe Lys Leu Glu Lys Asn Tyr Asn Leu Val Glu Ser Leu Lys Leu
CGA GAA GTG CTT CTG CCG AAA TTC AAG CTG GAG AAG AAC TAC AAT CTA GTG GAG TCC CTG AAG TTG
  1200                                                                  1250

400                                   410
Met Gly Ile Arg Met Leu Phe Asp Lys Asn Gly Asn Met Ala Gly Ile Ser Asp Gln Arg Ile Ala
ATG GGG ATC AGG ATG CTG TTT GAC AAA AAT GGC AAC ATG GCA GGC ATC TCA GAC CAA AGG ATC GCC
                                       1300

420                                    430
Ile Asp Leu Phe Lys His Gln Gly Thr Ile Thr Val Asn Glu Glu Gly Thr Gln Ala Thr Thr Val
ATC GAC CTG TTC AAG CAC CAA GGC ACG ATC ACA GTG AAC GAG GAA GGC ACC CAA GCC ACC ACT GTG
                     1350
```

-continued
Heparin Cofactor II

```
              440                                          450
Thr Thr Val Gly Phe Met Pro Leu Ser Thr Gln Val Arg Phe Thr Val Asp Arg Pro Phe Leu Phe Leu
ACC ACG GTG GGG TTC ATG CCG CTG TCC ACC CAA GTC CGC TTC ACT GTC GAC CGC CCC TTT CTT TTC CTC
    1400                                                      1450

460                                  470                                480
Ile Tyr Glu His Arg Thr Ser Cys Leu Leu Phe Met Gly Arg Val Ala Asn Pro Ser Arg Ser   °
ATC TAC GAG CAC CGC ACC AGC TGC CTG CTC TTC ATG GGA AGA GTG GCC AAC CCC AGC AGG TCC TAGAG
                                   1500

GTGGAGGTCTAGGTGTCTGAAGTGCCTTGGGGGCACCCTCATTTTGTTTCCATTCCAACAACGAGAACAGAGATGTT
         1550                                                 1600

CTGGCATCATTTACGTAGTTTACGCTACCAATCTGAATTCGAGGCCCATATGAGAGGAGCTTAGAAACGACCAAGAA
                           1650

GAGAGGCTTGTTGGAATCAATTCTGCACAATAGCCCATGCTGTAAGCTCATAGAAGTCACTGTAACTGTAGTGTGTC
         1700                                        1750

TGCTGTTACCTAGAGGGTCTCACCTCCCCACTCTTCACAGCAAACCTGAGCAGCGCGTCCTAAGCACCTCCCGCTCCG
                                   1800

GTGACCCCATCCTTGCACACCTGACTCTGTCACTCAAGCCTTTCTCCACCAGGCCCCTCATCTGAATACCAAGCACAG
     1850                                             1900

AAATGAGTGGTGTGACTAATTCCTTACCTCTCCCAAGGAGGGTACACAACTAGCACCATTCTTGATGTCCAGGGAAG
                       1950

AAGCCACCTCAAGACATATGAGGGGTGCCCTGGGCTAATGTTAGGGCTTAATTTTCTCAAAGCCTGACCTTTCAAAT
      2000                                              2050

CCATGATGAATGCCATCAGTCCCTCCTGCTGTTGCCTCCCTGTGACCTGGAGGACAGTGTGTGCCATGTCTCCCATAC
                               2100

TAGAGATAAATAAATGTAGCCACATTTACTGTGAAAAAAAAAAAAAAAAAAAAAAAAAAAAAAAA
2150                                            2200       2215
```

Various other examples will be apparent to the person skilled in the art after reading the present disclosure without departing from the spirit and scope of the invention. It is intended that all such other examples be included within the scope of the appended claims.

What is claimed is:

1. An isolated DNA sequence encoding for human heparin cofactor II with an amino acid substitution of arginine at position 444 for a leucine.

* * * * *

UNITED STATES PATENT AND TRADEMARK OFFICE
CERTIFICATE OF CORRECTION

PATENT NO. : 5,102,995

DATED : April 7, 1992

INVENTOR(S) : Douglas M. Tollefsen, Vivianna M. Derechin and Morey A. Blinder It is certified that error appears in the above-identified patent and that said Letters Patent is hereby corrected as shown below:

Column 4, lines 8 and 27 "●" should read --■--.

Signed and Sealed this

Fourteenth Day of September, 1993

Attest:

BRUCE LEHMAN

*Attesting Officer*     *Commissioner of Patents and Trademarks*